United States Patent [19]

Augurt

[11] Patent Number: 4,486,387
[45] Date of Patent: Dec. 4, 1984

[54] DISPOSABLE PREVACUUM STEAM STERILIZER TEST DEVICE

[75] Inventor: Thomas A. Augurt, Stamford, Conn.
[73] Assignee: Propper Manufacturing Co., Inc., Long Island City, N.Y.
[21] Appl. No.: 388,744
[22] Filed: Jun. 16, 1982
[51] Int. Cl.³ ............................................ G01N 21/78
[52] U.S. Cl. .................................... 422/58; 116/206; 422/26; 422/57; 422/119; 436/1
[58] Field of Search ...................... 422/26, 56, 57, 58, 422/59, 60, 61, 295, 119; 436/1, 38, 39; 116/206, 207, 216

[56] References Cited

U.S. PATENT DOCUMENTS

| | | | |
|---|---|---|---|
| 2,931,757 | 4/1960 | Rdzok et al. | 435/31 |
| 3,094,373 | 6/1963 | Luechauer | 8/137 |
| 3,239,429 | 3/1966 | Menolasino et al. | 435/296 |
| 3,337,416 | 8/1967 | Forgacs | 435/294 |
| 3,346,464 | 10/1967 | Ernst | 435/296 |
| 3,440,144 | 4/1969 | Anderson | 435/31 |
| 3,585,112 | 6/1971 | Ernst | 435/31 |
| 3,661,717 | 5/1972 | Nelson | 435/31 |
| 3,711,378 | 1/1973 | Kereluk | 435/31 |
| 3,846,242 | 11/1974 | Ernst | 435/31 |
| 3,862,824 | 1/1975 | Chapman | 422/56 |
| 4,087,326 | 5/1978 | Kereluk | 435/31 |
| 4,328,182 | 5/1982 | Blake | 422/56 |

OTHER PUBLICATIONS

Perkins, John J., "Prevacuum High Temperature Steam Sterilization", *Principles and Methods of Sterilization*, pp. 122–152.
"Good Hospital Practice: Steam Sterilization and Sterility Assurance", AAMI, pp. 9–10.
Bowie, J. H. et al., "The Bowie and Dick Autoclave Tape Test", *Lancet*, pp. 586–587, 1963.

*Primary Examiner*—Barry S. Richman
*Assistant Examiner*—B. P. Heaney
*Attorney, Agent, or Firm*—Amster, Rothstein & Engelberg

[57] ABSTRACT

A disposable test package for testing the proper functioning of a steam sterilizer is formed with a test sheet adapted to change color in response to the presence of steam under preselected sterilization conditions. The sheet is surrounded by disposable nonwoven porous material, above and below, forming a core region around the test sheet having desired height and porosity parameters and a shell region around the core having different height and porosity parameters which are adapted to permit the test pack to simulate a Bowie and Dick challenge pack for the testing of steam sterilizers.

5 Claims, 4 Drawing Figures

U.S. Patent   Dec. 4, 1984   4,486,387
FIG. 1.
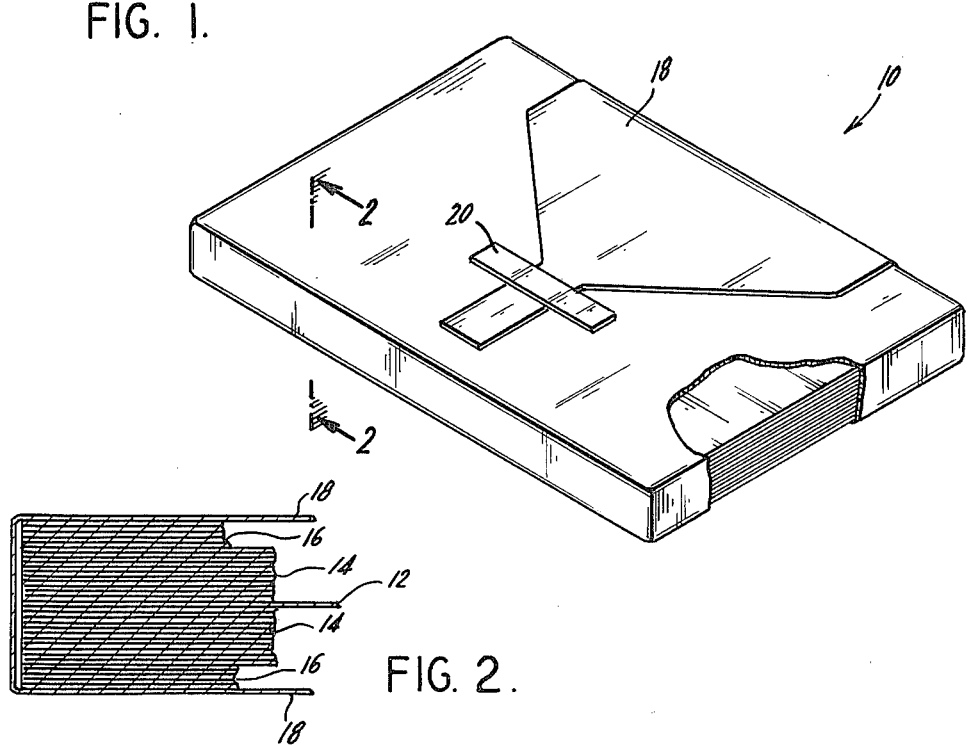
FIG. 2.
FIG. 3.
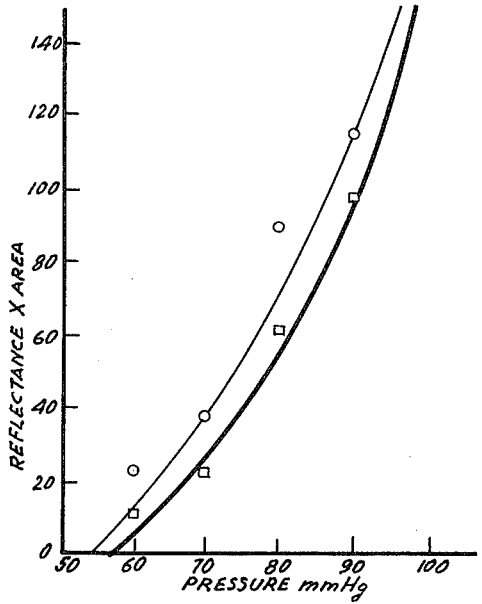
FIG. 4.
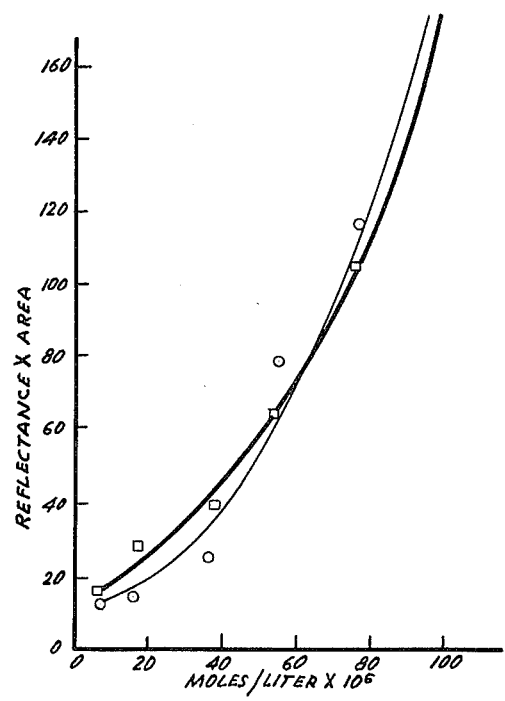

DISPOSABLE PREVACUUM STEAM STERILIZER TEST DEVICE

This invention relates generally to the sterilization of medical and surgical products and more specifically to a disposable test pack adapted to be processed through a conventional sterilization cycle in a prevacuum steam sterilizer to check the proper operation of the sterilizer.

In the sterilization of medical dressings and instruments by steam, such dressings or instruments are conventionally assembled in bundles or packs and placed in a steam sterilization chamber which is sequenced through an appropriate sterilization cycle. Individual packages may contain stacks of towels, dressings, sponges and similar materials or may contain desired compliments of surgical instruments or equipment for specific surgical procedures.

A current method of steam sterilization practice involves the placement of such packs in a sterilizer, the evacuation of air from the sterilizer and the introduction of saturated steam at a desired pressure to produce a desired temperature for a selected period of time. Prevacuum sterilizers operating in this manner have frequently replaced the downward displacement or gravity air discharge sterilizers previously used. The significant advantage of the prevacuum method is that removal of air before introduction of steam permits the rapid penetration of steam throughout the surgical pack. Elimination of air is necessary in all steam sterilizers since air trapped in the packages would prevent sterilization of the portion of the packs interior where it collected. With the prevacuum method, the time required for steam penetration in a typical sterilization cycle is greatly reduced and prevacuum sterilizers currently operate on a relatively short cycle (with an exposure time in the order of 3-4 minutes at 134° C.). The operation of such sterilizers is well described in, John J. Perkins, *Principles and Methods of Sterilization, in the Health Sciences* published by Charles C. Thomas, Springfield, Illinois, Chapter VI, "Prevacuum High Temperature Sterilization."

The ability to sterilize instruments in a shortened time, however, is dependent on the assumption that air is properly evacuated from the sterilizer. This includes the expectation that the vacuum system is functioning properly to evacuate the chamber initially and that there are no air leaks in the sterilizer or the vacuum lines which would permit introduction of air after the vacuum is drawn. During routine use, wear on certain sterilizer parts will eventually result in air leaks and there is a need to test the sterilizer on a periodic (daily) basis to ascertain that the vacuum system is functioning properly.

In 1961, a test procedure was proposed by J. Dick et al. and discribed by J. H. Bowie, et al. of the Department of Microbiology, Royal Infirmary, Edinburgh, Scotland in an article appearing in *The Lancet*, Mar. 16, 1963, pp. 586-587, which suggested a protocol for determining that the sterilizer was in proper working order, and that the vacuum system was operating properly. As indicated in the article, residual air in the system at the time steam is introduced will be swept by the steam pressure into the pack, usually to the pack center. Trapped air in the pack inhibits proper steam penetration.

According to the Bowie and Dick protocol, sterilization indicating tape was used in combination with a stack of surgical towels to test the working order of the sterilizer on a daily basis. Sterilizer indicating tape is an adhesive tape having printed on its top surface stripes of a sterilization indicator material which has the property of changing color, for example from white to black, upon exposure to steam at an appropriate temperature for an appropriate period of time. According to the Bowie and Dick protocol, such tape was placed on a fabric sheet in a cross configuration and the fabric sheet was placed within a stack of folded surgical towels. The entire assembly was placed within the sterilizer. The sterilizer was run through its usual cycle with an exposure time of three and one-half minutes at 133°-134° C., after which the tape cross was examined to determine whether steam had completely penetrated the towel stacks effectively. A uniform color change was indication of a pass and the presence of incompletely changed indicator color was a failure.

This protocol is currently in widespread use and is described in the Association For The Advancement Of Medical Instrumentation (AAMI) Recommended Practice: Good Hospital Practice for Steam Sterilization and Sterility Assurance published by the AAMI, 1901 North Ft. Myer Drive, Suite 602, Arlington, Va. 22209. As indicated in Paragraph 7.8 of that publication entitled "Prevacuum Sterilizer Residual Air Test" the test involves the use of 100% cotton huckaback towels, freshly laundered but not ironed (in view of the fact that excess dryness may affect the test results) folded in a 9"×12" configuration and piled 10"-11" high. The details of the Bowie and Dick procedure are described in the above-referenced Recommended Practice.

The testing of prevacuum sterilizers according to the Bowie and Dick protocol involves a number of important shortcomings. Firstly, the test is subject to individual execution by the sterilization section of the hospital on a daily basis and the various requirements of the Bowie and Dick protocol, namely the type of towels or other fabrics used, their condition, age and the like (all of which affect the significance of the test result) may very widely from day to day and from institution to institution. Secondly, the performance of the Bowie and Dick protocol is relatively inconvenient and costly in that the expense of laundering towels (which cannot be thereafter used wirhout relaundering) assembling the test arrangement and the like involve costly hospital labor. Additionally, certain hospitals have elected to eliminate laundry facilities entirely, utilizing only single use disposable fabrics for their procedures making the proper conduct of the Bowie and Dick protocol more inconvenient.

It is an object of the present invention to provide a test pack for use in prevacuum steam sterilizers to determine whether the sterilizer is functioning in accordance with proper standards. A related object of the invention is to provide a test pack which suitably simulates air evacuation and steam penetration conditions of the conventional pack described in the Bowie and Dick protocol so as to define an appropriate challenge for a residual air test in a prevacuum sterilizer.

A further object of the invention is to create a test pack for prevacuum sterilizers which provides a repeatable and consistent standard for testing the working order of the sterilizer from day to day and sterilizer to sterilizer. It is a further object of the invention to provide such a test pack which is inexpensive and disposable after a single use, and does not require assembly by hospital personnel, nor the use of hospital linen or laundries.

In accomplishing these and other objects in accordance with the present invention, a disposable test pack is composed of a sterilization test sheet having defined areas adapted to change color in response to the presence of steam under selected exposure conditions, surrounded by a set of disposable nonwoven porous sheets of material arranged in overlying relation above and below the test sheet. The innermost sheets of material form an inner core region around the test sheet and the remaining sheets form an outer shell region, with the porosity and bulk of the inner core region and the porosity of the outer shell region being selected so as to define a desirable challenge to the sterilizer.

The test pack is designed to be used according to the accepted Bowie and Dick protocol and to be placed in an otherwise empty sterilization chamber, sequenced through a predetermined cycle and removed. The pack is then opened and the interior test sheet examined for evidence of inadequate steam penetration, air bubbles and like defects. The presence of such defects indicates faults in the vacuum or other systems within the sterilization unit which require evaluation and repair. The test is intended to be performed on a daily basis with the interior test sheet forming a permanent record of such testing. The nonwoven sheet material and the remainder of the pack are disposed of after a single use.

Further objects, features and advantages of the present invention will be more fully appreciated by reference to the following detailed description of a presently preferred embodiment in accordance with the invention, when taken in conjunction with the appended drawings, wherein:

FIG. 1 is a perspective view, partially cut away, of a test pack in accordance with the present invention;

FIG. 2 is a partial sectional view on line 2—2 in FIG. 1;

FIGS. 3 and 4 are graphic showings of the relationship between test results conducted with applicant's test pack and test results conducted in accordance with the conventional test pack of the Bowie and Dick protocol.

Applicant's test pack 10 includes a sterilization test sheet 12 of a type known in the art. This sheet is generally a rectangular sheet of relatively porous paper which has printed on its top surface a steam sensitive ink in a test pattern designed to cover a substantial portion of the sheet surface. An appropriate test sheet for this purpose is the Once-A-Day test sheet manufactured by Propper Manufacturing Co., Inc. of 36-04 Skillman Avenue, Long Island City, New York. This test sheet is shown in U.S. Pat. No. Des. 222,516.

The ink areas of this sheet are adapted to change color from white to black upon exposure to steam at a desired temperature for a desired period. The color change from white to black occurs over a period of time so that insufficiency of steam exposure may result in only partial development of the ink from white to black. This partial change may result in white or brown or lightened areas, visible on the test sheet. Test sheets of this type are generally known in the art and have been used in place of the cross sterilization tape strips described in the initial Bowie and Dick test procedure.

Applicant's new test pack 10 is designed to permit the use of a test sheet such as the Once-A-Day sheet without the use of the conventional stacks of cotton towels in accordance with the Bowie and Dick protocol. As indicated on the literature on the Bowie and Dick protocol, various types of defects are most frequently found in sterilization equipment. Principal among these are (1) inadequacy of initial vacuum, leaving residual air within the packs and (2) air leaks within the chamber or vacuum system which permit the re-entrainment of air after a vacuum has been drawn. In designing a test pack to evaluate both these types of flaws, as well as others, it was discovered that there are a variety of different constraints operating.

For example, to the extent a flaw is present in the vacuum system which prevents a sufficient vacuum from being formed in the first instance, a test pack having a low porosity and/or high bulk is more likely to reveal a flaw of this type than one having a high porosity and/or lower bulk. As the vacuum is drawn, the air within the test pack tends to be drawn out of the pack. Low porosity and/or very bulky material surrounding the test sheet would tend to increase the difficulty of removal of such air and increase the likelihood that the test pack would indicate a flaw.

On the other hand, flaws caused by leaks involve the introduction of air into the sterilizer after the vacuum has been drawn. In this situation, the relationship between the porosity of the material surrounding the test sheet and sensitivity of the test is the reverse. The less porous and/or more bulky the material surrounding the test sheet, the less likely it is that air introduced into the sterilizer after the vacuum has been drawn (as in the case of a leak) will re-enter the test pack. Accordingly, with respect to a flaw resulting from air leaks after a sufficient vacuum has been drawn, low porosity material surrounding the test sheet would tend to make it more difficult for air from such leak to enter the pack and decrease the likelihood that such a test pack would indicate a flaw.

In order to properly test the sterilizer, a test pack must balance these conflicting needs and provide appropriate challenge to either common type of flaws. Such a proper test pack is the currently accepted standard based on 10–11 inch stacks of folded cotton huchaback towels in accordance with the Bowie and Dick protocol. It is desirable to design a relatively small, inexpensive and disposable test pack which achieves a challenge to the sterilizer comparable to the challenge provided by the accepted Bowie and Dick protocol.

Applicant has found that a test pack can be fabricated which provides detection of the common sterilizer flaws in a manner comparable to the Bowie and Dick protocol by establishing a package of individual sheets of disposable material above and below an appropriate test sheet. Such sheets are assembled to form an inner core region adjacent the test sheet, and a shell region above and below the core region, with the thickness and porosity of the core region and the porosity of the shell region being selected according to desired parameters.

The preferred construction of applicant's test pack shown in FIG. 1 includes a conventional test sheet 12 surrounded by stacked sheets of nonwoven material of selected weight and porosity. In the preferred embodiment two types of material are used, with the first type forming the inner core region 14 and the second forming the shell region 16.

The entire package is then wrapped with an appropriate porous wrapping material 18 and taped 20 to form a sealed unit. The porosity of the wrapping material is such that it does not affect the test.

In the preferred embodiment, the shell region (16) is composed of five sheets of filter paper above and below an inner core region wherein each sheet has an appropriate basis weight of 214 lbs. (per 3,000 square feet) and an appropriate thickness of 0.02 inches per sheet. This material has a Frazier porosity of approximately 0.5–1.5 cu. ft./sq. ft./min. per sheet.

Frazier porosity is the measure of air permeability of sheet material as measured by the Frazier Differential Pressure Air Permeability Measuring Machine manufactured by Frazier Precision Instrument Company, Inc. of 210 Oakmont Avenue, Gaithersburg, Md. 02760. These measures of porosity are based on the differential pressure principle as measured by manometers. The porosity measure is given in cubic feet of air per square foot per minute at 0.5 inches of water pressure.

Another common measure of porosity of sheet material is the Gurley method which provides a measure of the time required for 100 ml. of air to pass through one square inch area of the specimen material at a pressure. Obviously, the Frazier porosities given herein in cubic feet per square foot per minute could be expressed by other standards of measurement.

The sheets in the core region (14) of the preferred embodiment of FIG. 1 include 11 sheets above and 11 sheets below the test sheet, each sheet comprising filter paper having an approximate basis weight of 64 lbs. (per 3,000 sq. ft.) and a thickness of approximately 0.02 inch. This material has a Frazier porosity of 75–95 cu. ft./sq. ft./min. per sheet.

In the preferred example, the height of this core region is 0.22 inch above and 0.22 inch below the test sheet and the total porosity of the sheets in the core region on each side of the test sheet is approximately 6.9–8.7 cu. ft./sq. ft./min. In the preferred example, the shell region has a thickness of 0.1 inch on each side of the core region and a Frazier porosity of approximately 0.1–0.3 cu. ft./sq. ft./min. on each side of the core.

The test pack, sheets and test sheet are preferably 9"×12", although other dimensions could be employed with possible alteration in other parameters.

Applicant has found that the porosity of stacked material of the type herein used is substantially linear so that if an individual sheet of material has a Frazier porosity of 90 cu. ft./sq. ft./min. a stack of ten sheets of such material will have a porosity 1/10 that of the individual sheet or 9 cu. ft./sq. ft./min.

Applicant has found that by forming a shell area having a relatively low porosity as compared with the core area, the number of sheets and height of the test pack can be significantly reduced with attendant economies of material and reduction in cost. Applicant has found that it is preferred that the stacked sheets of material in the core region of the pack on each side of the test sheet have a combined Frazier porosity of greater than 1.5 cu. ft./sq. ft./min. Applicant has also found that it is preferred that the stacked sheets of material in the core region of the pack on each side of the test sheet have a height of at least 0.03 inch. Applicant has also found that a shell area having a Frazier porosity of less than 0.5 cu. ft./sq. ft./min is desirable.

As indicated previously, it is desirable that the disposable test pack respond to faults in the sterilizing equipment in a manner comparable to cotton towels prepared in accordance with the Bowie and Dick protocol. Applicant's preferred embodiment accomplishes this desired objective.

Specifically, tests have been conducted in a specially modified prevacuum steam sterilizer altered to create conditions equivalent to sterilizer defects in a controlled and reproducable manner. The prevacuum steam sterilizer included a manually controlled vacuum pump, permitting alteration in the degree of vacuum drawn in the system, and an adjustable volume piston driven air injector. Incomplete air removal was simulated by evacuating the chamber up to 60 millimeters of mercury in a single step and omitting any subsequent evacuation. Air leaks in the sterilizer were simulated by adjusting the stroke of the injector piston to deliver a specified amount of air into the chamber during a normal steam exposure cycle following a satisfactorally complete evacuation of air.

The test sheet of applicant's preferred test pack is intended normally to be evaluated visually in the normal manner for such devices employed in the Bowie and Dick protocol. For purpose of quantifying applicant's tests, color changes in the chemical indicator sheet were evaluated by a reflectometer with a 10 millimeter orifice setting (Model XL-20 Gardener/Neotec Instrument Division of Pacific Scientific, Silver Spring, Md.). Using a green filter this instrument measured reflectance of color changes from white to black and was used in accordance with methods prescribed by The American Society For Testing And Materials (ASTM 1977). The upper limit of the reflectant scale was measured at 79 for an unexposed white sheet using the commercial Propper, Once-A-Day test sheet and 8.5 for a completely exposed black sheet. Surface area of the incompletely exposed portion of the test sheet was measured by calculating the area of the ellipse that best described the perimeter of the incompletely exposed area.

Applicant's tests revealed that in the range of reaction of primary interest, the effects of the two common flaws on the test sheets were substantially the same for applicant's disposable test pack and a test sheet prepared in accordance with the conventional Bowie and Dick protocol. Applicant gathered data with respect to the surface area of the undeveloped portion of the test sheet and the reflectance at the center of the indicator sheet within the undeveloped area. Measured data are as follows:

| Partial Vacuum Test | Applicant's Pack | | Towel Pack | |
| --- | --- | --- | --- | --- |
| | Area | Color | Area | Color |
| 55 mm Hg. | 0 | 8.5 | 0 | 8.5 |
| 60 mm Hg. | 1.25 | 9.4 | 2.375 | 9.9 |
| 70 mm | 1.75 | 12.2 | 2.625 | 14.8 |
| 80 mm | 4.38 | 13.8 | 3.375 | 25.8 |
| 90 mm | 6.80 | 14.7 | 4.70 | 25.7 |
| 100 mm | 72.25 | 42.9 | 8.44 | 69.4 |

| Air Injection Test (Moles Of Air Injected/leter of sterilizer volume | Applicant's Pack | | Towel Pack | |
| --- | --- | --- | --- | --- |
| | Area | Color | Area | Color |
| $8.8 \times 10^{-6}$ | 1.2 | 11.4 | 1.2 | 10.3 |
| $17.5 \times 10^{-6}$ | 2.4 | 12.2 | 1.7 | 10.3 |
| $38.2 \times 10^{-6}$ | 3.2 | 12.9 | 2.0 | 13.8 |
| $55.6 \times 10^{-6}$ | 5.1 | 13.5 | 4.9 | 11.4 |
| $78.2 \times 10^{-6}$ | 6.6 | 16.5 | 5.85 | 20.5 |
| $101 \times 10^{-6}$ | 10.3 | 19.3 | 6.9 | 32.8 |

As the above data indicates, the product of the measured surface area of the faults in applicant's tests multiplied by the reflectance of the test sheet center for the disposable test pack is equivalent to the same product for the conventional of Bowie and Dick protocol. This relationship is shown in FIGS. 3 and 4. FIG. 3 shows reflectance multiplied by area plotted versus the degree of vacuum (indicated in millimeters of mercury) in the sterilizer before the introduction of steam. FIG. 4 shows a similar comparison for the data gathered based on simulated air leaks with the reflectance times area being plotted against the volume of air injected in Moles per liter if sterilizer volume times $10^6$.

As indicated in the data presentation of FIGS. 3 and 4 the reflectance multiplied by area measure for applicant's test pack and the conventional Bowie and Dick protocol closely follow one another.

The foregoing is considered as illustrative only of the principles of the invention. Further, since numerous modifications and changes will readily occur to those skilled in the art, it is not desired to limit the invention to the exact construction and operation shown and described and accordingly all suitable modifications and equivalents may be resorted to falling within the scope of the invention as defined by the following claims.

What is claimed is:

1. A disposable test pack for evaluation of prevacuum steam autoclaves comprising a sterilization test sheet having defined areas adapted to change color in response to the presence of steam under preselected sterilization conditions, variations in degree of said color change indicating variations in sterilization parameters, a first set of disposable nonwoven porous sheets arranged in overlaying relation positioned above and immediately adjacent the upper face of said sterilization test sheet, a second set of disposable nonwoven porous sheets arranged in overlaying relation and positioned below and immediately adjacent the lower face of said sterilization test sheet, the inner most sheets of said first and second sets forming an inner core region of said test pack adjacent said sterilization test sheet, said inner core region having a selected height and a porosity which is different from the porosity of the remainder of the test pack so that the test pack simulates the air entrapping qualities of a Bowie and Dick challenge pack, and means for retaining said first and second sheet sets in close proximity above and below, respectively, said test sheet.

2. A disposable test pack for evaluation of prevacuum steam autoclaves comprising a sterilization test sheet having defined areas adapted to change color in response to the presence of steam under preselected sterilization conditions, variations in degree of said color change indicating variations in sterilization parameters, a first set of disposable nonwoven porous sheets arranged in overlaying relation positioned above and immediately adjacent the upper face of said sterilization test sheet, a second set of disposable nonwoven porous sheets arranged in overlaying relation and positioned below and immediately adjacent the lower face of said sterilization test sheet, the inner most sheets of said first and second sets forming an inner core region of said test pack adjacent said sterilization test sheet, said inner core region having a selected height and porosity, and means for retaining said first and second sheet sets in close proximity above and below, respectively, said test sheet wherein said inner core region constitutes material having a combined Frasier porosity of greater than 1.5 cu. ft./sq. ft./min. and a height of at least 0.03 of an inch.

3. A disposable test pack for evaluation of prevacuum steam autoclaves comprising a sterilization test sheet having defined areas adapted to change color in response to the presence of steam under preselected sterilization conditions, variations in degree of said color change indicating variations in sterilization parameters, a first set of disposable nonwoven porous sheets arranged in overlaying relation positioned above and immediately adjacent the upper face of said sterilization test sheet, a second set of disposable nonwoven porous sheets arranged in overlaying relation and positioned below and immediately adjacent the lower face of said sterilization test sheet, the inner most sheets of said first and second sets forming an inner core region of said test pack adjacent said sterilization test sheet, said inner core region having a selected height and porosity, and means for retaining said first and second sheet sets in close proximity above and below, respectively, said test sheet wherein said disposable nonwoven porous sheets outside of said inner core region constitute a shell region of said disposable test pack, the sheets of said shell region having a combined Frasier porosity of less than 0.5 cu. ft./sq. ft./ins.

4. A disposable test pack for evaluation of prevacuum steam autoclaves comprising a sterilization test sheet having defined areas adapted to change color in response to the presence of steam under preselected sterilization conditions, variations in degree of said color change indicating variations in sterilization parameters, a first set of disposable nonwoven porous sheets arranged in overlaying relation positioned above and immediately adjaent the upper face of said sterilization test sheet, a second set of disposable nonwoven porous sheets arranged in overlaying relation and positioned below and immediately adjacent the lower face of said sterilization test sheet, the inner most sheets of said first and second sets forming an inner core region of said test pack adjacent said sterilization test sheet, said inner core region having a selected height and porosity, and means for retaining said first and second sheet sets in close proximity above and below, respectively, said test sheet wherein said sheets of disposable nonwoven porous material defining said inner core region includes at least two sheets having a first predetermined porosity and said sheets of disposable nonwoven porous material outside of said inner core region includes at least two sheets of a second predetermined specific porosity different from said first predetermined porosity.

5. A disposable test pack for evaluation of prevacuum steam autoclaves comprising a sterilization test sheet having defined areas adapted to change color in response to the presence of steam under preselected sterilization conditions, variations in degree of said color change indicating variations in sterilization parameters, a first set of nonwoven disposable porous sheets arranged in overlaying relation positioned above and immediately adjacent the upper face of said sterilization test sheet, a second set of nonwoven disposable porous sheets arranged in overlaying relation and positioned below and immediately adjacent the lower face of said sterilization test sheet, the inner most sheets of said first and second sets forming an inner core region of said test pack adjacent said sterilization test sheet, the outer sheets of said first and second sets forming a shell region of said disposable test pack, the overall porosity of said shell region being lower than the overall porosity of said core region, and means for retaining said disposable test pack as an assembled unit.

* * * * *